US009377359B1

(12) United States Patent
Wittmann et al.

(10) Patent No.: US 9,377,359 B1
(45) Date of Patent: Jun. 28, 2016

(54) OPTICAL MEASURING SYSTEM AND GAS DETECTING METHOD

(71) Applicant: Axetris AG, Kaegiswil (CH)

(72) Inventors: Andreas Wittmann, Giswil (CH); Marc-Oliver Zufferey, Alpnachstaad (CH); Urs Boegli, Esslingen (CH); Kai Hassler, Lucerne (CH)

(73) Assignee: Axetris AG, Kaegiswil (CH)

( * ) Notice: Subject to any disclaimer, the term of this patent is extended or adjusted under 35 U.S.C. 154(b) by 0 days.

(21) Appl. No.: 14/613,482

(22) Filed: Feb. 4, 2015

(51) Int. Cl.
*G01N 21/00* (2006.01)
*G01J 3/45* (2006.01)
*G01J 3/28* (2006.01)
*G01J 3/44* (2006.01)

(52) U.S. Cl.
CPC ................. *G01J 3/45* (2013.01); *G01J 3/2803* (2013.01); *G01J 3/4412* (2013.01)

(58) Field of Classification Search
CPC ............ H01S 5/02296; H01S 5/02212; G01N 2001/064; G01N 21/3504; G01J 3/4531; G01J 3/4338; G01J 3/42; G01J 3/0262
See application file for complete search history.

(56) References Cited

U.S. PATENT DOCUMENTS

| 4,934,816 | A | 6/1990 | Silver et al. | |
|---|---|---|---|---|
| 8,003,945 | B1 * | 8/2011 | Wong | G01J 5/0014 250/343 |
| 2005/0242359 | A1 * | 11/2005 | Yoshida | H01S 5/02212 257/99 |
| 2006/0098202 | A1 * | 5/2006 | Willing | G01N 21/3504 356/437 |
| 2010/0002235 | A1 * | 1/2010 | Willing | G01N 21/3504 356/437 |

* cited by examiner

*Primary Examiner* — Kara E Geisel
*Assistant Examiner* — Maurice Smith
(74) *Attorney, Agent, or Firm* — Von Rohrscheidt Patents

(57) ABSTRACT

An optical measuring system and a method for gas detection, the optical measuring system including a light emitter and at least one light detector arranged in at least one housing, wherein the light emitter emits a modulated main light beam with a mean wave length $\lambda_0$ with a modulation span $\Delta\lambda$. At least one opto-mechanical component, e.g. a housing window including optically effective boundary surfaces, is arranged between the light emitter and the light detector and causes scatter light beams which interfere with the main light beam so that self-mixing occurs and/or etalons are caused. According to the invention the at least one opto-mechanical component is arranged relative to the light emitter and/or the light detector at an optimized distance L which is a function of the wave length $\lambda_0$ and the modulation span $\Delta\lambda$ of the main light beam.

17 Claims, 9 Drawing Sheets

OPTICAL MEASURING SYSTEM AND GAS DETECTING METHOD

FIELD OF THE INVENTION

The invention relates to an optical measuring system and a method for gas detection, the optical measuring system including a light emitter and at least one light detector forming optical components arranged in at least one housing, the at least one housing optionally including housing windows forming opto-mechanical components and/or other opto-mechanical components, wherein the opto-mechanical components include optically effective boundary surfaces, wherein the light emitter emits a modulated main light beam with a mean wave length $\lambda_0$ with a modulation span $\Delta\lambda$, wherein at least one scatter light beam of the main light beam that is partially reflected/scattered at least at one optically effective boundary surface of at least one opto-mechanical component from the main light beam in a direction of the light emitter and/or light detector causes self-mixing in the light emitter and/or etalons at the light detector through interference with the main light beam, wherein the interference causes an interfered main light beam so that a measuring signal of the light detector includes an interfering signal portion and a main signal portion, wherein the interfering signal influences a demodulated measuring signal of the light detector.

BACKGROUND OF THE INVENTION

Optical measuring systems of this type are being used for various measuring tasks like e.g. for length measuring or spectroscopy. In measuring systems of this type typically a laser diode is used as a light emitter and a suitable photo diode is used as a light detector. Laser absorption spectroscopy is used for example for gas detection. Thus, the main light beam emitted by the light emitter is detected by the light detector after passing through a gas or gas mix and a received signal is provided to a signal analyzer, in particular a lock in amplifier for evaluation. The signal analyzer separates constant interference patterns from the measuring signal of the light detector. However, the signal analyzer cannot completely eliminate time variable interference patterns from the received signal so that the detection sensitivity for the gas to be detected is significantly reduced due to the increased noise. Among other influences temperature influences trigger time variable interference patterns wherein the temperature influences change a length of an optical path for the main light beam from the light emitter to the light detector. Furthermore reflections and/or scattering of the main light beam at inner surfaces of the housing of the measuring system or at boundary surfaces of beam forming and/or beam directing optical or opto-mechanical components arranged in the housing like e.g. lenses or mirrors or at an inner or outer surface of the housing window can cause interference patterns of this type. The reflections or the scatterings can cause scatter light beams that are directed to the light emitter and/or the light detector. Scatter light beams of this type cause self-mixing in the light emitter and/or etalons at the light detector in that they interfere with the main light beam forming interference patterns and in that they form an interfered main light beam which is received by the light detector. These interference patterns are also a function of temperature and can therefore change over time. Self-mixing and etalons are caused by different length optical paths of the scatter light beams from the optical and/or opto-mechanical component respectively partially reflecting the main light beam up to the light emitter or the light detector relative to the optical path length of the main light beam. For the etalons a distance of the reflecting or scattering optical and/or opto-mechanical component up to the light detector is relevant, for the self-mixing the distance of the respective component up to the aperture of the light emitter is relevant, which component forms a "receiver" for the scatter light beam entering through the aperture into the resonator and which interferes with the main beam that is partially reflected back at an inside of the laser.

In laser absorption spectroscopy for gas detection often a wave length modulation method is used. Thus, the wave length and typically also the intensity of the main light beam of the light emitter, for example of a continuously tunable diode laser is modulated with a frequency f wherein the wave length is varied over a possible absorption spectrum of a sample to be analyzed. The laser light is absorbed by the gas sample when the wave length of the light corresponds to a resonance frequency of the gas or when it is varied relative to the resonance frequency. When the main light beam after passing the gas sample impacts the light detector, e.g. a photo diode, the output signal of the light detector includes AC voltage components at the modulation frequency f and at the superimposing higher harmonic frequencies mf wherein m is a natural positive number. The demodulation of the output signal of the light detector at a harmonic frequency mf moves the measurement to a higher frequency band mf with lower 1/f noise which can improve measuring sensitivity of the optical measuring system.

When using lasers as light emitters due to the relatively large coherence length in particular an occurrence of interferences between the main light beam originating from the light emitter and of scatter light beams which are generated by undesirable reflections or scattering of the main light beam is particularly disadvantageous. Thus two different phenomena have to be differentiated. The phenomenon of influencing light emission by radiation that is back coupled into the laser aperture of the laser and which is known as self-mixing has a particularly strong effect upon the measurement since the back coupled radiation is amplified in the laser. In practical applications the main cause for the self-mixing is often found to be the scattering or reflection of the main light beam at the housing window which is provided for an exit of the main light beam and which protects the laser light emitter from environmental impacts like e.g. contamination or ambient humidity. Through the scattering this phenomenon is also present for inclined housing windows since a portion of the light can be directly or indirectly, for example through scattering at the housing inner wall, back coupled into the laser aperture. Other surfaces which are further remote from the aperture of the light emitter can also cause self-mixing, e.g. the reflection/scattering at the photo diode. Typically, however, their influence is lower. The second phenomenon that occurs in optical measuring systems is caused by interferences on the detector which are caused by different optical wave lengths of the main beam and the scatter beam and which are designated as etalons. Etalons like self-mixing are caused by scatter light beams at all optical and opto-mechanical components in the measuring system which then interfere with the main light beam at the detector. In order to minimize a falsification of the measuring signal of the light detector and thus of the measuring values by self-mixing and/or etalons either the self-mixing or the etalons themselves have to be reduced or their influence upon the measuring value has to be minimized.

In order to reduce these interferences various measures are known in the art. Among them are in particular rendering all housing windows non reflective, making the housing windows wedge shaped and a tilted, this means inclined arrangement of the housing windows in the beam path in order to prevent scattering as much as possible or in order to deflect the scattering out of the main light beam which scattering could cause interferences with the main light beam and thus self-mixing. Furthermore absorbing coatings in the housing of the optical measuring system and/or apertures arranged in the beam path can reduce reflections and scattering. In spite of these effective measures not all reflections and scatterings of the main light beam can be prevented which leads to self-mixing which typically has a very strong negative interference influence upon the measuring signal of the light detector in optical systems with coherent radiation. During operations the housing windows and surfaces of such optical measuring systems become contaminated quite frequently, e.g. by dust or condensation. This contamination greatly increases scattering of the main light beam and the interferences recited supra increase over the service life of the system. Thus, it is advantageous for the service life of such optical measuring systems to set the system up so that unavoidable contaminations affect the measuring signal of the system as little as possible.

When measuring spectra interferences recited supra are typically visible as periodic signals which are designated as "fringes" in the art. Self-mixing and etalons lead to a distortion of the measured gas absorption line for tunable diode laser spectroscopy systems (TDLS) which cannot be eliminated simply by calibration or computational methods. Thus, periodic interferences with a period in an order of magnitude of a width of the measured absorption line are particularly disadvantageous.

In principle the phenomenon self-mixing can be greatly reduced with an optical insulator. Unfortunately good quality insulators for non-telecom wave lengths are very expensive so that they are rarely used in industrial applications. It is furthermore appreciated that the optical insulator itself also has optical interfaces, wherein the optical interface of the optical insulator which optical interface is oriented towards the laser can also cause self-mixing by reflection/scattering. Persson proposes an "intensity referencing" method which reduces the effect of self-mixing while using balanced detection. However, this only achieves interference amplitude reductions by a factor of 10 (applied physics B87, 523-530 (2007)). Webster describes a very simple method to prevent etalons in that he inserts a coplanar tilted plate into a portion of the optical path wherein the coplanar plate is transparent for a laser wave length. Periodic pivoting of the tilted plate during the measurement facilitates that the interfering signal is averaged out due to the periodically changing optical path length. This solution helped to reduce the interfering signal by a factor of 30 (Opt. Soc. Am. B2 1464 (1985)). In order to prevent wear of mechanically moved components which leads to an increase in service life of the sensor piezo based actuators can be used. These, however, only facilitate generating small path length differences, wherein these elements are only effectively useable for averaging interferences with a very small free spectral range compared to a gas absorption line width. Silver and Stanton use for example a piezo electrical transducer (U.S. Pat. No. 4,934,816) which varies a longitudinal deflection of the mirror of a multi path cell and thus averages out the interferences based on the mirror arrangement. Piezo electrical transducers of this type, however, are typically rather expensive. Reid et alias have shown that it is possible by mixing an additional frequency into the modulation signal which frequency is slower than the modulation frequency, to average out such interferences also without changing the optical path lengths (Appl. Opt. 19, 3349-3354, 1980)). This principle, however, is only useable for interferences with a very small free spectral range since averaging has to be performed over at least one period. Almost the same result, however, can be achieved through low pass filtering, e.g. by using signal averaging in the data processing. Thus, the free spectral range has to differ significantly from a width of the gas absorption line. Otherwise also the absorption signal is influenced during the averaging. The preceding solutions are typically only useable specifically for a particular problem in an efficient manner. For example an optical insulator in front of the laser will only provide suppression of self-mixing but not suppression of etalons on the detector. Most of the cited solution proposals aim to reduce interferences in an averaged measuring signal of the detector.

BRIEF SUMMARY OF THE INVENTION

Improving upon the prior art described supra it is an object of the invention to provide an option how to significantly reduce an influence of an interfering signal of the light detector upon the demodulated measuring signal so that the main signal is clearly detectable in the measuring signal and so that measuring sensitivity of the optical measuring system is significantly improved.

The object is achieved according to the invention by an optical measuring system with the features of the independent patent claim 1 and by the features of the independent patent claim 9. Further advantageous embodiments can be derived from the dependent patent claims.

The invention is based on the core idea to use a particularity of the wave length modulation spectroscopy method (WMS) in order to adapt interferences in the measuring signal of the light detector using an adaptation of the distances in the measuring system upon the modulation span of the light detector so that interferences in the measuring signal of the light detector are not transferred into the demodulated signal (e.g. into the 2f signal) in order to reduce interferences. Through an intelligent choice of the distance in the measuring system thus in principle all dominant interferences in the demodulated measuring signal can be suppressed or at least reduced.

According to the invention at least one of the optical and/or auto mechanical components of the measuring system is arranged relative to another optical and/or auto mechanical component so that the spatial orientation and/or the distance L of optically effective boundary surfaces of the optical and/or opto-mechanical components relative to one another yield an optical path length which cause the free spectral range with a period $\Lambda$ of the measuring signal which is selected so that using the provided modulation span $\Delta\lambda$ of the modulated main light beam with the wave length $\lambda_0$ cancels or at least minimizes the effect of the interference upon the measuring signal of the demodulated signal for all phases. The period $\Lambda$ is generated by the interference of the main signal with the interfering signal. This means that the respective distances and the modulation span $\Delta\lambda$ are adapted to each other. The modulation span $\Delta\lambda$ is defined as the peak to peak amplitude of the modulation signal which can have any form of modulation. This affects the any optical and/or opto-mechanical components at which reflections or scattering can occur while forming scatter light beams which propagate in a direction of the light emitter and/or light detector and which scatter light beams are directed to the light detector. The at least one scatter light beam is considered part of the non-interfered or of the interfered main light beam. Thus, the main light beam and also the occurring scatter light beams start in the aperture of the light emitter since the scatter light beams are split off from the main light beam in the partial reflection/scattering of the main light beam.

The invention advantageously relates to an optical measuring system, including a laser diode as a light emitter, and a photo diode as light detector forming optical components of the measuring system and including at least one housing window arranged between the light emitter and the light detector and including devices for controlling the light emitters and for signal processing of the measuring signals of the light detectors. The light emitter, the light detector and the at least one housing window for passing the main light beam through form optical and/or opto-mechanical components of the measuring system wherein the light emitter and the light detector are arranged in a common housing with a housing window or in separate housings respectively including a light permeable housing window. The measuring system can also include additional optical, opto-mechanical and/or mechanical components or elements in addition to the light emitter, light detector and the at least one housing window wherein the components are arranged within or outside of the at least one housing of the optical measuring system. These can be for example mirrors for folding the beam path or a gas cell provided with windows into which the gas substance to be examined is introduced. Thus, the light emitter emits a modulated main light beam with a mean wave length $\lambda_0$ with a modulation span $\Delta\lambda$. Typically the light emitter is wave length modulated with a mean wave length $\lambda_0$ with the defined modulation span $\Delta\lambda$ with the frequency f and a demodulation of the signal received by the light detector is performed. The modulation can be performed with any wave shape, for example with a triangular or a cosine shaped wave form. In practical applications the light emitter is advantageously modulated with a point symmetrical wave form, wherein the modulation form includes uneven Fourier components (1f, 3f, 5f, etc.). Typically the Fourier component of the measuring signal, this means of the measuring signal for the two-, four- and/or m-fold modulation frequency is determined so that m=2, 4, 6, . . . which is intended to suppress the portion of the amplitude-modulation in the measuring signal. In a practical application typically the Fourier-component of twice the modulation frequency or for an even integer multiple m of the modulation frequency is determined. When the Fourier-component for the twice the frequency is measured this yields the so called 2f-signal, four times the frequency yields the 4f-signal, etc.

According to the core idea of the invention a relative positioning or orientation of the optical and/or opto-mechanical components in the beam path is optimized where undesirable reflections or scattering can occur wherein the optimization is performed with respect to a position of the light emitter and also the light detector in the optical measuring system so that occurring interferences have a minimum effect upon the measuring signal. Thus, in particular a distance of the housing window from the light emitter and advantageously from the light detector is selected so that an influence of the cited effects is minimal. Additionally also distances of additional optical and/or opto-mechanical components from one another or from the light emitter and/or the light detector can be selected so that the interferences caused by them have a minimum effect upon the measuring signal that is put out and demodulated by the light detector.

In principle there are two options that are independent from each other to reduce the recited interferences by optimizing the position of the optical and/or opto-mechanical elements in the beam path. On the one hand side a suitable choice of a distance that is as large as possible between an optical and/or mechanical component of the optical measuring system and the aperture of the light emitter facilitates increasing the traveled optical path length of the scatter light beam so that the power that is coupled back into the aperture of the light emitters (self-mixing) is reduced, in particular in case that the reflection or scatter has a diffuse character. Thus, in particular the increase in the optical path length leads to a reduced interfering signal portion of the measured signal. In case the reason for the reflected scatter light beam is in punctiform scatter elements (dust, scratches, etc.) typically a diffused character of the scatter light is generated at which the power typically decreases proportional to $(1/l)^2$ (l=distance). Thus, for example an increase of a distance between the aperture of the light emitter and the remote optical or opto-mechanical components like windows, lenses, mirrors and similar can reduce the size of the interfering signal with respect to the portion of the main signal in the measuring signal. The same applies also for mechanical and/or opto-mechanical components like apertures, inner housing components etc. which are touched or impacted by the main light beam.

On the other hand side besides diffuse scatter also a scatter with non-diffuse character can be achieved by a suitably selected specially defined distance between the optical and/or opto-mechanical and/or mechanical components of the optical measuring system according to the invention so that an influence of the interfering signal upon the measuring signal which is put out by the light detector which is interfered with by self-mixing or etalons is reduced when it impacts the light detector. The interfering signal of the measuring signals typically includes a number of interfering signal components which are caused by reflections or scatterings at the different optical and/or opto-mechanical and/or mechanical components of the optical measuring system, wherein the respective scatter light beams form a scatter light beam bundle which extends in a direction of the light emitter or light detector. By tuning the distances of the respective components relative to each other it can be achieved that the respectively considered Fourier-component of the respective interfering signal of the scatter light beam bundle can be reduced, this means the Fourier-component of the selected demodulation frequency for selected modulation span $\Delta\lambda$ disappears or is at least greatly reduced.

Quite frequently the housing window of the at least one housing of the optical measuring system in which the light emitter and/or light detector are arranged is the main reason for scatter light beams of the main light beam which interfere with the main light beam to form an interfered main light beam and thus cause a measuring signal which includes an interfering signal portion and a main signal portion wherein the interfering signal is coupled with the main signal. This applies independently from the light emitter and the light detector being arranged in separate housings or in housing sections of a common housing which are offset from one another for the light emitter and also for the light detector. Consequently according to the invention the distance between the light emitter, the at least one housing window and/or the light detector or between the light detector, the at least one housing window and the light emitter and thus the optical path length for the main light beam and/or the at least one scatter light beam is selected so that the period $\Lambda$ of the interfering signal caused by these components in the measuring signal fulfills the conditions stated supra.

As stated supra the optical measuring system according to the invention for gas detection includes a light emitter, a light detector and at least one housing window. Optimum distances between two of these optical and/or opto-mechanical components of the optical measuring system, advantageously between the light emitter and the at least one housing window and/or light detector can be empirically determined or computed for each selected wave form by which the main light beam is modulated.

During empirical determination of advantageous distances the distance between two respective optical or opto-mechanical components of the optical measuring system is varied in small increments and the measuring signal put out by the light detector is demodulated wherein for example a Fourier-component of the measuring signal for twice the modulation frequency is determined. Thus, distances can be determined at which the Fourier-component of the selected demodulation frequency disappears or is at least greatly reduced. At these locations the demodulated measuring signal essentially includes the main signal, in that impacts of the interfering signals upon the main signal are greatly reduced.

When computing favorable distances L between two respective optical or opto-mechanical components of the optical measuring system like e.g. the light emitter and the housing window or the light detector and the housing window it can be presumed that the components together form a "Fabry Perot etalon" with low finesse. For computing the optical path length difference $\Delta S$ a differentiation has to be made between the phenomena self-mixing and etalons. Subsequently in the computation S1 designates the optical path length from the light emitter to a reflector and the optical path length from the reflector to the light detector. This relates to a symmetrical arrangement in which the optical path length from the light emitter to the light detector is 2*S1 based on which the invention described. It is apparent that the different optical path lengths add up for a non symmetrical arrangement, this means for a different distance of the emitter and the detector from the reflector. In order to describe the invention subsequently a non interfered main light beam, an interfered main light beam and a scatter light beam are used, wherein the main light beam depending on the configuration covers the path length S1 and the scatter light beam covers partial paths lengths S1', S1'', S1''' etc.

In the subsequent description the phenomena "self-mixing" and "etalons" are described separate from each other for reasons of simplicity though they can also occur simultaneously. The subsequent formulas respectively only describe one phenomenon or another phenomenon.

In case of etalons the main light beam and the scatter light beam cover different optical paths starting from the aperture of the light emitter which interfere at the detector to form the interfered main light beam. An optical path length difference of the main light beam relative to the at least one interfering scatter light beam is thus computed as $\Delta S = |S_{Scatter} - S_{Main}|$. In case a portion of the main light beam is reflected at the photo diode surface of the light detector and then reaches the detector again from the housing window of the light detector that is at a distance L, the optical path length difference $\Delta S = |S_{Scatter} - S_{Main}|$ equals twice the distance between the photo diode and the housing window of the light detector. This yields $\Delta S = |S_{Scatter} - S_{Main}| = |(2*S1 + 2*S1') - 2*S1| = 2*S1' = 2L$ as path length difference, wherein 2*S1 represents the distance between the aperture of the light emitter and the detector surface and S1' corresponds to the distance L of the housing window of the light detector from the light detector.

In case of self-mixing the interference occurs between the scatter light beam that is coupled back into the aperture of the light emitter and the non-interfered main light beam within the light emitter, for example of a laser so that the respectively interfered main light beam exits from the aperture of the light emitter. Since in case of self-mixing the non-interfered main light beam is completely arranged within the light emitter $S_{Main}=0$ has to be presumed for self-mixing and this yields the optical path length difference $\Delta S = |S_{Scatter} - S_{Main}| = |S_{Scatter} - 0| = S_{Scatter}$, which is solely defined by the path of the scatter light beam outside of the aperture of the light emitter. In case the light is scattered back directly by the housing window of the light emitter the traveled optical path of the scatter light beam $S_{Scatter}=2L$, thus twice the distance between the aperture of the light emitter and the impact point of the main light beam at the housing window and thus $\Delta S = S_{Scatter} = 2L$. When the light is reflected back into the aperture of the light emitter indirectly, e.g. through a housing wall the path of the scatter light beam extends accordingly.

The transmission spectrum of an arrangement of this type has narrow transmission-maxima at "Fringes" for wave lengths which satisfy resonance criteria, whereas other spectral ranges are completely canceled during transmission. This is done through constructive or destructive interference of light beams running in the resonator or detector. In this context it is appreciated that there are no real "Fabry-Perot Etalons" in the optical measuring system according to the invention since the configuration provides that there are no parallel surfaces. However, a fringe can also be caused by scatter light beams. The rules that apply for parallel resonator surfaces and which are known from the Fabry Perot Etalon can be transferred analogously to inclined resonator surfaces and can thus also be used for the optical measuring system according to the invention.

The distance of the transmission maxima from each other is designated as free spectral range of the (FSR) and designated as $\Lambda$. This free spectral range $\Lambda$ is a function of the optical path length difference $\Delta S$, between the main light beam and the at least one scatter light beam on the light detector. It is well known that the free spectral range $\Lambda$ is computed as:

$$\Lambda = \frac{\lambda_0^2}{\Delta S},$$

wherein $\lambda_0$ is the mean wave length of the modulated main light beam.

The following general relationship applies for the amplitude A of the interfering signal of the light detector of the optical measuring system according to the invention which is a function of the optical path length difference:

$$A_{detector} = A_{fringe} \cos\left(\frac{2\pi}{\Lambda}\lambda + \psi_{fringe}\right).$$

This is based on a maximum amplitude $A_{fringe}$ and a phase $\psi_{fringe}$

The modulation of the light emitter can be described by the formula:

$$\lambda = \lambda_0 + \frac{\Delta\lambda}{2} \cdot \text{waveform}(2\pi ft)$$

wherein wave form is the form of modulation and f the modulation frequency for the main light beam. Thus, amplitude A of the AC portion of the instant demodulated measuring signal of the light detector is defined by the following formula:

$$A_{detector}(t, \lambda_0, \Delta\lambda) = A_{fringe} \cos\left(\frac{2\pi}{\Lambda} \frac{\Delta\lambda}{2} \cdot \text{waveform}(2\pi f t) + \psi'_{fringe}\right)$$

Wherein the following applies for the phase:

$$\psi'_{fringe} = \psi_{fringe} + \frac{2\pi\Delta S}{\lambda_0}.$$

The Amplitude A of an exemplary lock-in-reference signal for the instant 2f-signal is computed according to the formula:

$$A_{lockin,2f}(t) = A_{lockin} \cos(4\pi f t)$$

In general, this means for all mf-signals, this means for 2f-, 4f-, 6f-Signals etc. the formula reads as follows:

$$A_{lockin,mf}(t) = A_{lockin} \cos(2\pi m f t)$$

The employed lock-in-amplifier multiplies the Light detector signal $A_{detector}(t,\lambda_0,\Delta\lambda)$ with the reference signal $A_{lockin,2m}(t)$ and subsequently integrates a number of N periods, wherein a measuring time per period is inversely proportional to the modulation frequency f. This yields the followoing relationship for an mf-signal for the Amplitude A:

$$A_{mf}(\lambda_0) = \frac{f}{N}\int_0^{t=\frac{N}{f}} A_{detector}(t, \lambda_0, \Delta\lambda) \cdot A_{lockin,mf}(t)dt.$$

The optical path length difference $\Delta S$ is now selected so that for a modulation signal with given wave form and modulation span $\Delta\lambda$ the formula provided supra is minimized for all possible phases $\psi'_{fringe}$ $A_{mf}$ or so that $A_{mf}=0$.

Analyitically the computation is very complex depending on the wave fomr but numerically it is very simple to perform. The preceding formulas apply for all phases and are thus independent from setting the phase, this means a phase relationship between the main light beam and the at least one scatter light beam.

As a consequence the Fourier-component of the demodulated measuring signal of the order 2f, 4f, 6f, etc. has a curve that is a function of the distance L of the respective optical or opto-mechanical components, wherein the amplitude of the interfering signal in the demodulated measuring signal at certain distances caused by precisely defined optical path length differences $\Delta S$ of the Main light beam and of the at least one scatter light beam becomes zero. When the optical path length difference $\Delta S$ of the main light beam and of the at least one scatter light beam is not optimal this yields a demodulated measuring signal that is a function of the phase.

When distance L is optimized the demodulated measuring signal of the light detector is not a function of the phase. Thus, for example temperature induced phase changes have no effect or only have a strongly reduced effect upon the demodulated measuring signal.

An intensity curve that is a function of distance has adjoining hump shaped intensity portions which include a main maximum with a highest amplitude-peak and a number of intermediary maxima respectively with reduced amplitude-peaks. The position of the main maximum relative to the intermediary maxima is a function of the order of the demodulated mf-measuring signal that is being used. For a 2f-signal the main maximum starts as a first portion at the zero point of the coordinate system, wherein the intermediary maxima adjoin at the right at the main maximum. For the 4f-signal an additional intermediary maximum is arranged between the zero point and the main maximum and for a 6f-signal two intermediary maxima are arranged on a left side of the main maximum and so forth. The position of the main maximum is defined according to the order m/2 of the demodulation measuring signal that is being used. For a 2f-signal the main maximum forms the first hump of the intensity curve, for a 4f-signal it forms the second hump and for a 6f-Signal it forms the third hump of the intensity curve etc. The width of the intermediary maxima $\Delta X$ is determined by the mean wave length $\lambda_0$ and the modulation span $\Delta\lambda$. This yields the width of the main maximum at $2*\Delta X$. The distance L is now selected so that the optical path length difference $\Delta S$ of the main light beam to the at least one scatter light beam is proportional to the width $\Delta X$, this means it is a multiple thereof. The minima, zero points, of the intensity curve of this type, not considering the two zero points defining the main maximum, have a distance $\Delta X$ from each other.

Advantageously already a significant reduction of the impact of the interfering signal upon the main signal in the measuring signal is reached when the optical path length difference $\Delta S$ through a suitable choice of the distance L between the optical and/or opto-mechanical components is greater than $0.5*\Delta X*(m+1)$, with $m=2, 4, 6, \ldots$, according to the order 2f, 4f, 6f, $\ldots$ of the measuring signal that is being used.

Generally the following applies for the optimum optical distance L of the optical and/or opto-mechanical components relative to one another at which distance the interfering signal is canceled out at an order m of the demodulated measuring signal that is being used for the optical path length difference $\Delta S$ the relationship holds: $\Delta S = n*\Delta X$, with $n=1, 2, 3, \ldots$, and with $n \neq m/2$, wherein n is a natural integer greater 0 with $m=2, 4, 6, \ldots$, according to the order 2f, 4f, 6f, $\ldots$ of the measuring signal that is being used. The limitation to $n \neq m/2$ excludes that with respect to a 2f-signal n cannot be 1, with respect to a 4f-signal n cannot be 2, and with respect to a 6f-signal n cannot be 3, etc. Thus, the intensity portion with the highest amplitude-peak is excluded, this means the main maximum is excluded which has a double width relative to the adjacent intermediary maxima. Thus, $\Delta X$ is defined as the smallest distance of the minima of the intensity curve. The reason is when allowing that $n=m/2$, the worst case occurs, this means the interfering signal is at a maximum in this case. When processing the 2f-signal this case occurs for $n=1$ ($m=2$) and thus for $\Delta S = \Delta X$. For this reason $\Delta S > \Delta X$ should be selected since the interfering signal decreases significantly between $\Delta S = \Delta X$ and $\Delta S = 2*\Delta X$.

The statements provided supra relate to the optimum tuning of the distance L for canceling the interfering signal. In practical applications it may suffice to minimize the interfering signal by allowing a bandwidth about the zero points. This means that n is not an integer for $\Delta S = n*\Delta X$. The condition with $n=1, 2, 3, \ldots$ is only used for finding locations where the interfering signal is minimal or zero.

In advantageous embodiments of the invention with any modulation form of the main light beam optical and/or opto-mechanical components are arranged relative to one another and/or the light emitter so that $\Delta S$ is greater than 0.8-times or less than 1.2-times $n*\Delta X$, with $n \neq m/2$ and with $m=2, 4, 6, \ldots$, according to the order 2f, 4f, 6f, $\ldots$ of the measuring signal that is being used. A sufficient reduction of the self-mixing and of the etalons can already be used when the distance of the optical and/or opto-mechanical components is selected so that $\Delta S$ is greater than 0.7-times or less than 1.3-times $n*\Delta X$, with $n \neq m/2$ and with $m=2, 4, 6, \ldots$, according to the order 2f, 4f, 6f, $\ldots$ of the measuring signal that is being used.

In one embodiment of the invention the main light beam is modulated with a triangular wave form. Thus, for minimization or canceling of the effect of the interfering signals upon the main signal in the measuring signal a suitable distance L of the optical and/or opto-mechanical components relative to one another is obtained when $\Delta S=n*\Delta X$, with $\Delta X=\lambda_0^2/\Delta\lambda$, wherein the limitation applies that $n\neq m/2$.

The respectively reviewed Fourier-component disappears for example for a triangular modulation always when the optical path length difference $\Delta S=n*\Delta X=n*\lambda_0^2/\Delta\lambda$, wherein n=1, 2, 3, is a natural integer greater zero. Thus, it is furthermore appreciated that $n\neq m/2$ is selected and m=2, 4, 6, ..., according to the order 2f, 4f, 6f ... of the measuring signal that is being used.

For the triangular modulation form and a demodulation with 2f the distance L is advantageously selected so that the period $\Lambda$ of the demodulated measuring signal corresponds to half the modulation span $\Delta\lambda$ of the main light beam. Thus, in the formula $\Delta S=n*\lambda^2/\Delta\lambda$ n=2 is selected. In case of further remote optical or opto-mechanical components the period $\Lambda$ is selected so that a multiple $n\Lambda$ of the period $\Lambda$ corresponds to the modulation span $\Lambda\lambda$.

In an embodiment of the invention with a triangle shape modulation of the main light beam the optical and/or opto-mechanical components ca be arranged relative to one another and/or relative to the light emitter so that due to the selected distance the period $\Lambda$ is less than 0.8-times the modulation span $\Delta\lambda$ or a multiple $n\Lambda$ of the period $\Lambda$ is greater than 0.8 times or less than 1.2 times the modulation span $\Delta\lambda$ of the main light beam, with $n\neq m/2$ and with m=2, 4, 6 and so forth. A sufficient reduction of the self-mixing and of the etalons can already be achieved when the distance L of the optical and/or opto-mechanical components is selected so that a multiple $n\Lambda$ of the period $\Lambda$ is greater than 0.7 times or less than 1.3 times the modulation span $\Delta\lambda$, also with $n\neq m/2$ and m=2, 4, 6 etc.

In one embodiment of the invention $\Delta S$ corresponds to the twice the distance L between the light emitter and the housing window ($\Delta S=2L$), since the dominant scatter radiation is scattered back on a direct path to the light emitter and scatterings via the housing wall can be neglected (blackened inner wall of the housing).

In a most favorable embodiment of the invention a distance of an inside of the housing window to the light emitter and/or of the inside of the housing window of the light detector to the light detector is typically 8 mm, advantageously 10 mm, further advantageously at least 15 mm. This minimum distance provides that a significant reduction of the effect of the interfering signal upon the main signal in the measuring signal is achieved since the optical path length difference $\Delta S$ is provided significantly greater than $0.5*\Delta X*(m+1)$. The provided distance relates to the distance of the housing window to the aperture of the light emitter (Laser diode) or to the chip surface of the light detector (Photo diode).

Scattering of the main light beam originating at the light emitter occurs independently from the thickness of the housing window always at the two boundary surfaces of the housing window of the light emitter, thus on an inside and on an outside, wherein two interfering signals are created which can interfere with main signal in the light emitter (laser cavity) which leads to a modulation of the radiation exit power. The same holds for scatter light beams at the housing window of the detector, wherein the scatter light beam interferes with the main light beam impacting the detector surface. Accordingly it is useful to position the light emitter, the light detector and an inside of the housing window relative to one another so that the Fourier-component of the interfering signal caused by the inside disappears. Thus, only the interfering signal caused by the outside of the housing window can still interfere with the main signal. In order to achieve that the instant Fourier component also loses the interfering signal that is caused by the outside of the housing window it is required that the distance of the outside of the housing window from the light emitter/-detector also complies with the conditions recited supra with respect to the period $\Lambda$ of the interfering signal of the measuring signal. This can be achieved through a suitable choice of the thickness of the housing window. Thus, this distance of the outside from the inside of the housing window determined by the thickness also complies with the requirements with respect to the period $\Lambda$ of the interfering signal of the measuring signal. When a contamination of the inside the housing window can be excluded in an alternative the design can only be adapted to the outside of the housing window.

All measures recited supra are effective when modulating the main light beam with any wave form. Besides modulating the main light beam with a triangular wave form also the modulation of the main light beam with a cosine shaped wave form has proven advantageous. The modulation with a triangular wave form is more effective and thus more advantageous than the modulation with the cosine shaped wave form when scatter light beams of optical or opto-mechanical components that are further away shall be suppressed.

It is appreciated that also measures that are known in the art can be provided for avoiding scatter light beams or for reducing their intensity in the optical measuring system according to the invention for measuring a spectrum, like for example a housing window that is placed at a slant angle relative to the beam path, anti-reflection coatings on the housing window, wedge shaped windows, blackening of the inside of the housing, an optical insulator in the beam path and an active temperature sink for the light emitter and optionally a passive temperature sink for the housing, in order to make the optical path length for the main light beam and optionally the occurring scatter light beams as much temperature independent as possible.

BRIEF DESCRIPTION OF THE DRAWINGS

Subsequently the invention is described in more detail based on an embodiment illustrated in the drawing figure. Additional features of the invention can be derived from the subsequent description of an embodiment of the invention in combination with the appended drawing figures, wherein.

DETAILED DESCRIPTION OF THE INVENTION

Figure 1:
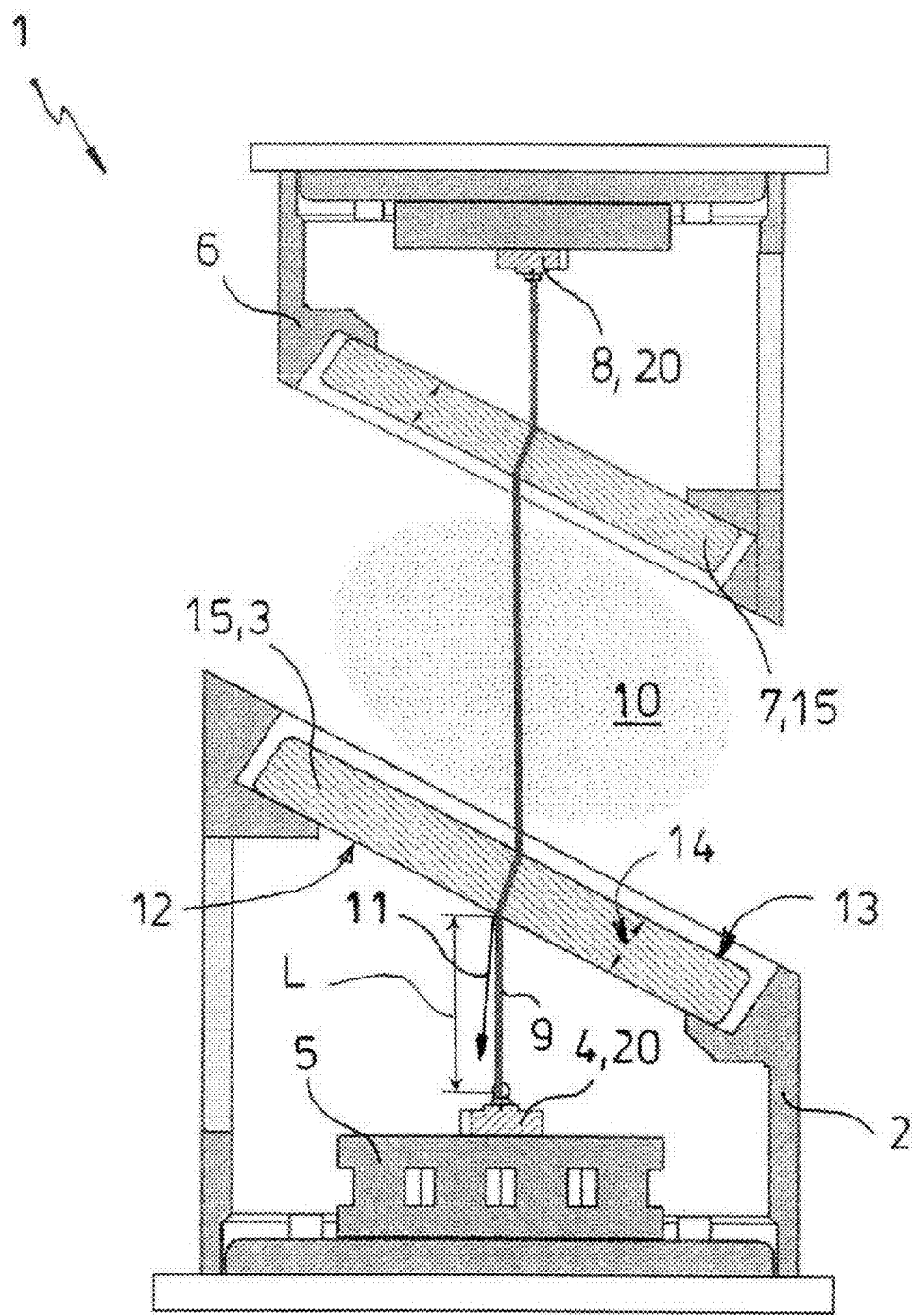
FIG. 1 illustrates an optical measuring system according to the invention with a first housing with an inclined housing window and with a laser diode arranged therein as a light emitter, and with a second housing with an inclined housing window and with a photo diode arranged therein as a light detector.

FIG. 1 illustrates an optical measuring system 1 according to the invention for measuring a spectrum during gas detection, the optical measuring system including a first housing 2 with an inclined light permeable housing window 3 in which a laser diode is arranged as a light emitter 4 on an active temperature sink 5. The measuring system 1 furthermore includes a second housing 6 that is separate from the housing 2 and includes an inclined housing window 7 in which a light detector 8 is arranged. The two housings 2, 6 are arranged at a distance from each other, opposite to each other and in alignment with each other. The light emitter 4 and the light detector 8 form the optical components 20 of the illustrated measuring system 1. A main light beam 9 is emitted by the light emitter 4 wherein the main light beam is centrally oriented towards the housing window 3. The main light beam 9 exits the housing 2 and penetrates a gas or gas mix 10 that is arranged between the housing 2 with the light emitter 4 and the housing 6 with the light detector 8. Before it enters through the housing window 7 into the housing 6 with the light detector 8. The housing 2 and the housing 6 are arranged relative to each other so that the emitted main light beam 9 after passing through the gas or the gas mix 10 impacts the light detector 8. In the embodiment illustrated in FIG. 1 the dominating interference is caused by reflection or scattering of the main light beam 9 at the housing window 3. The light emitter 4 is advantageously configured as a laser diode with a laser aperture arranged in a direction towards the housing window 3. The main light beam 9 is for example partially reflected at a window inside 12 of the housing window 3 wherein the occurring scatter light beam 11 is coupled into the light emitter 4 so that it causes self-mixing at this location. In principle, however, this applies for all reflecting or scattering surfaces and also for the beam paths with plural reflections or scatterings as long as the back coupled scatter light beams 11 return back into the active zone of the light emitter 4.

Figure 7A:
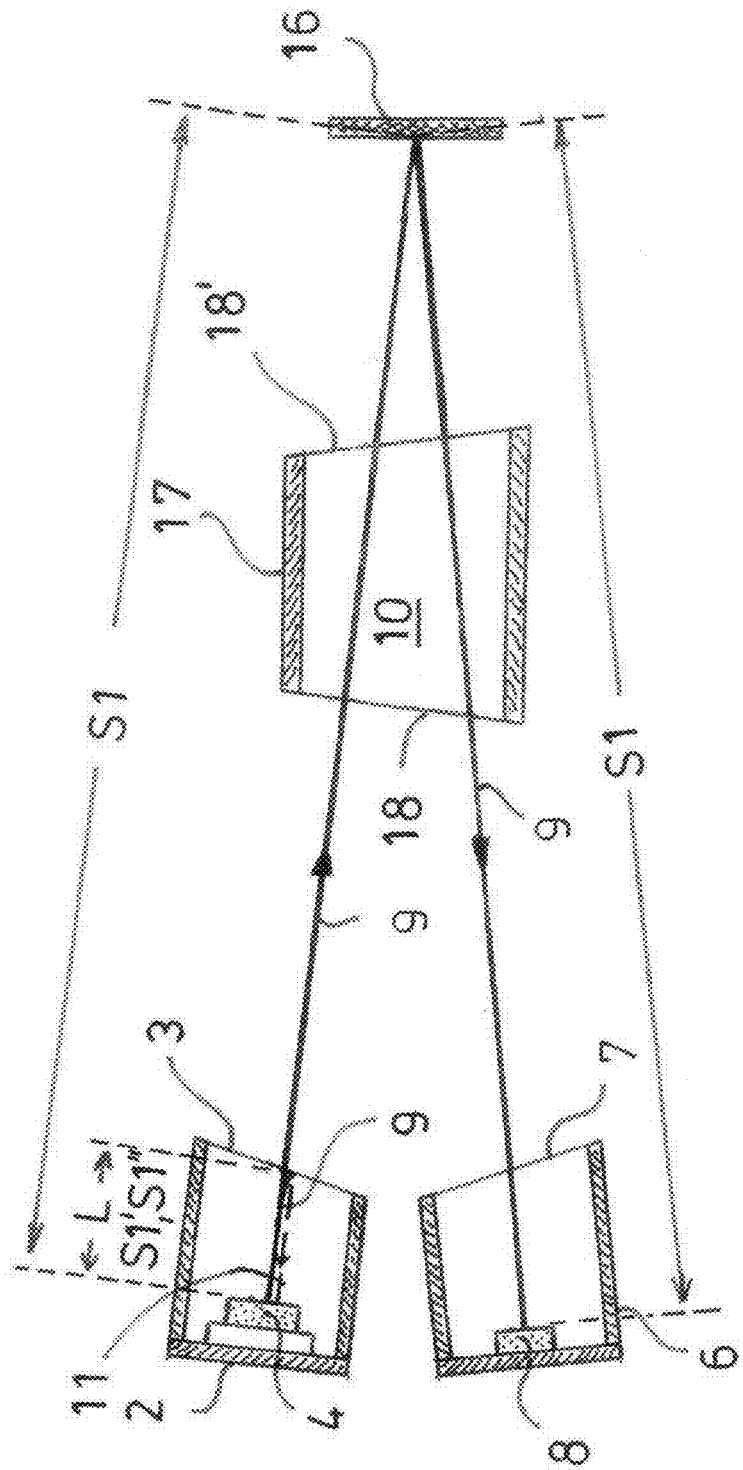
FIGS. 7a-7d illustrate a schematic of a path of the scatter light beam for direct back scatted-reflection (FIG. 7a) from the housing window of the light emitter into the laser aperture (self-mixing effect) and indirect back scatter/-reflection (self-mixing) from the housing window through a housing wall into a laser cavity (FIG. 7b) and the path of the main light beam and the scatter light beam when scattering occurs at the gas cell inlet window and interference of the two light beams occurs at the light detector (FIG. 7c) and back scatter from the aperture of the photo diode to the housing window of the light detector and direct back scatter to the photo diode (FIG. 7d) and a resulting etalon on the detector.
Figure 7B:
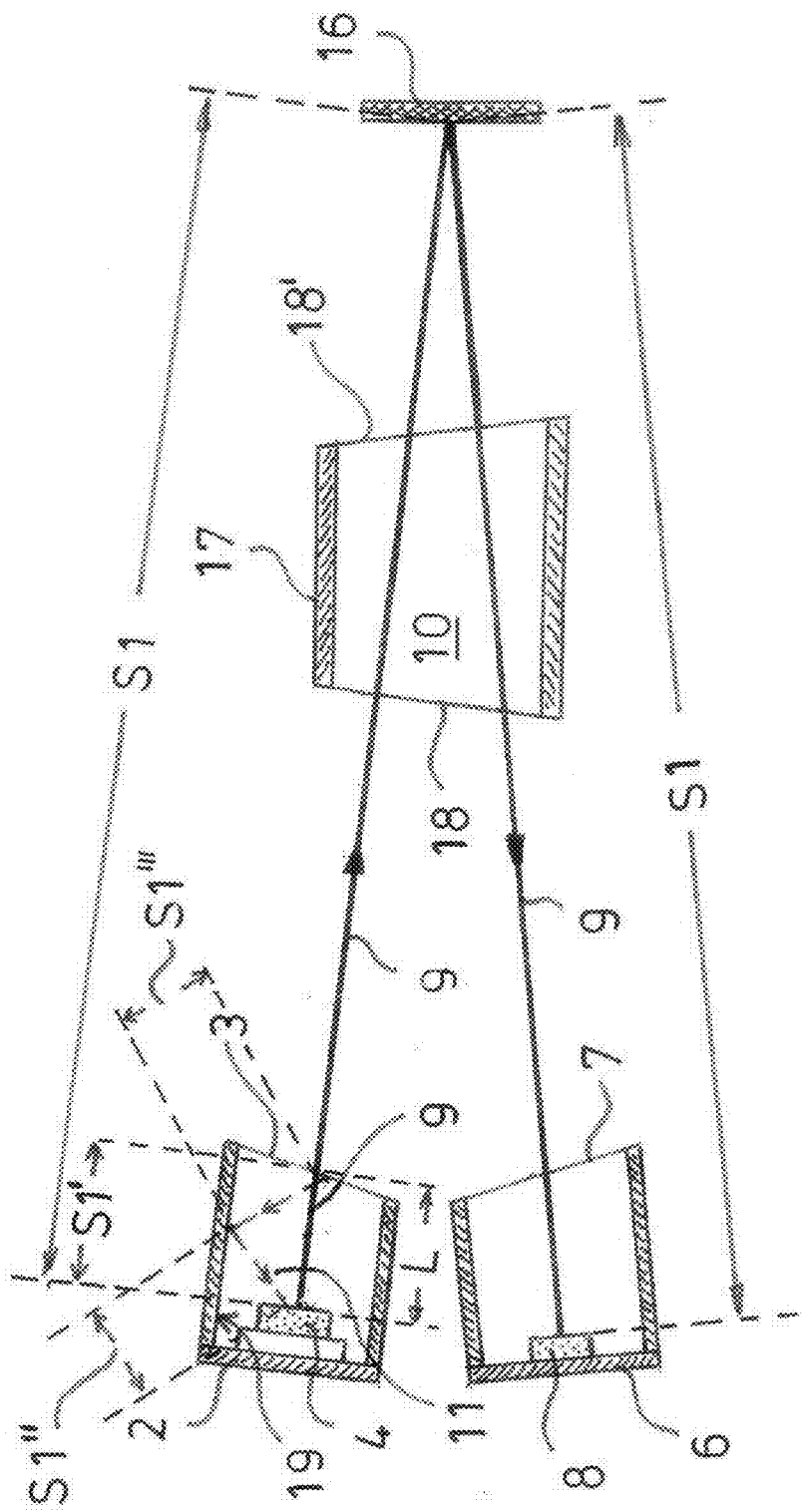
Figure 7C:
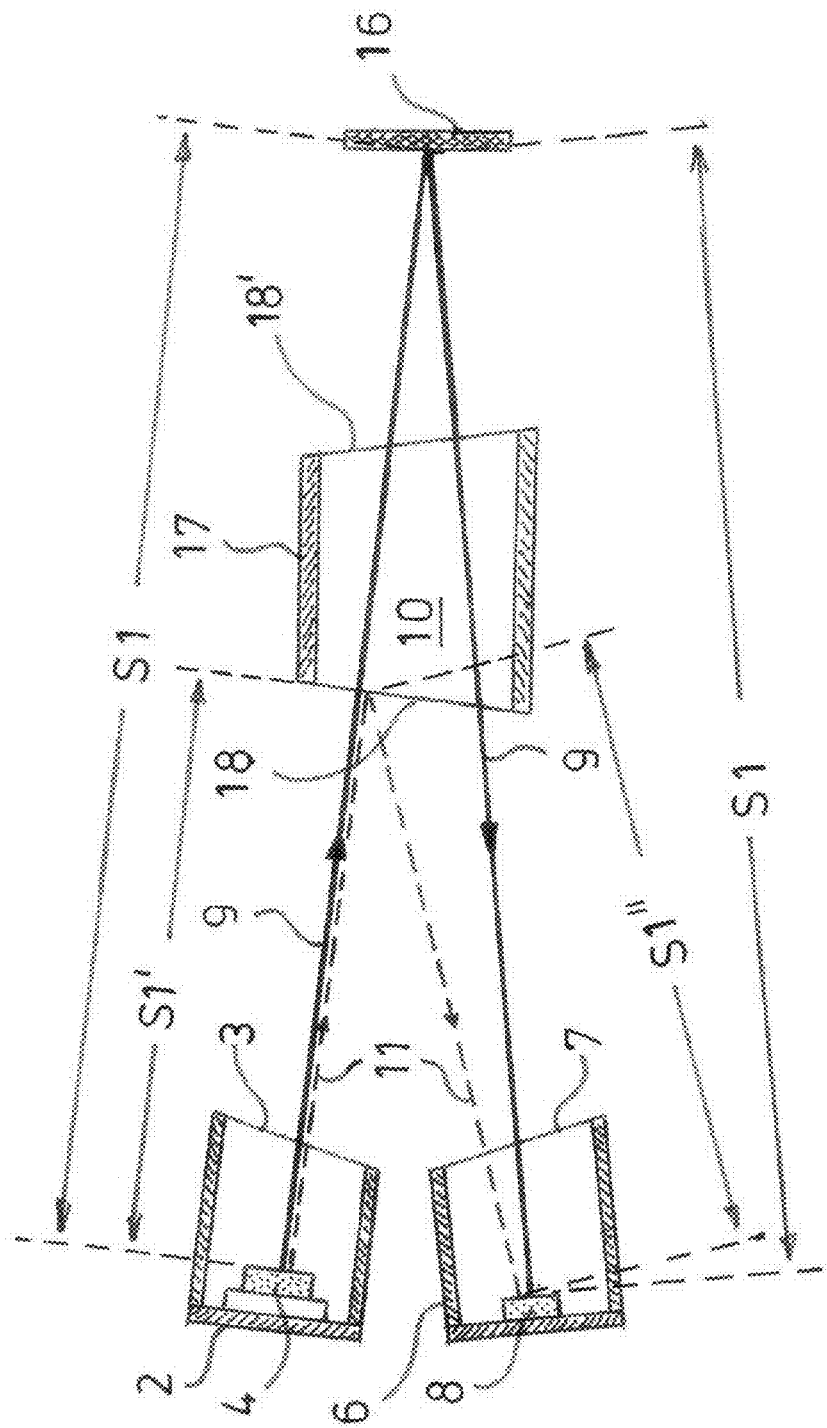
Figure 7D:
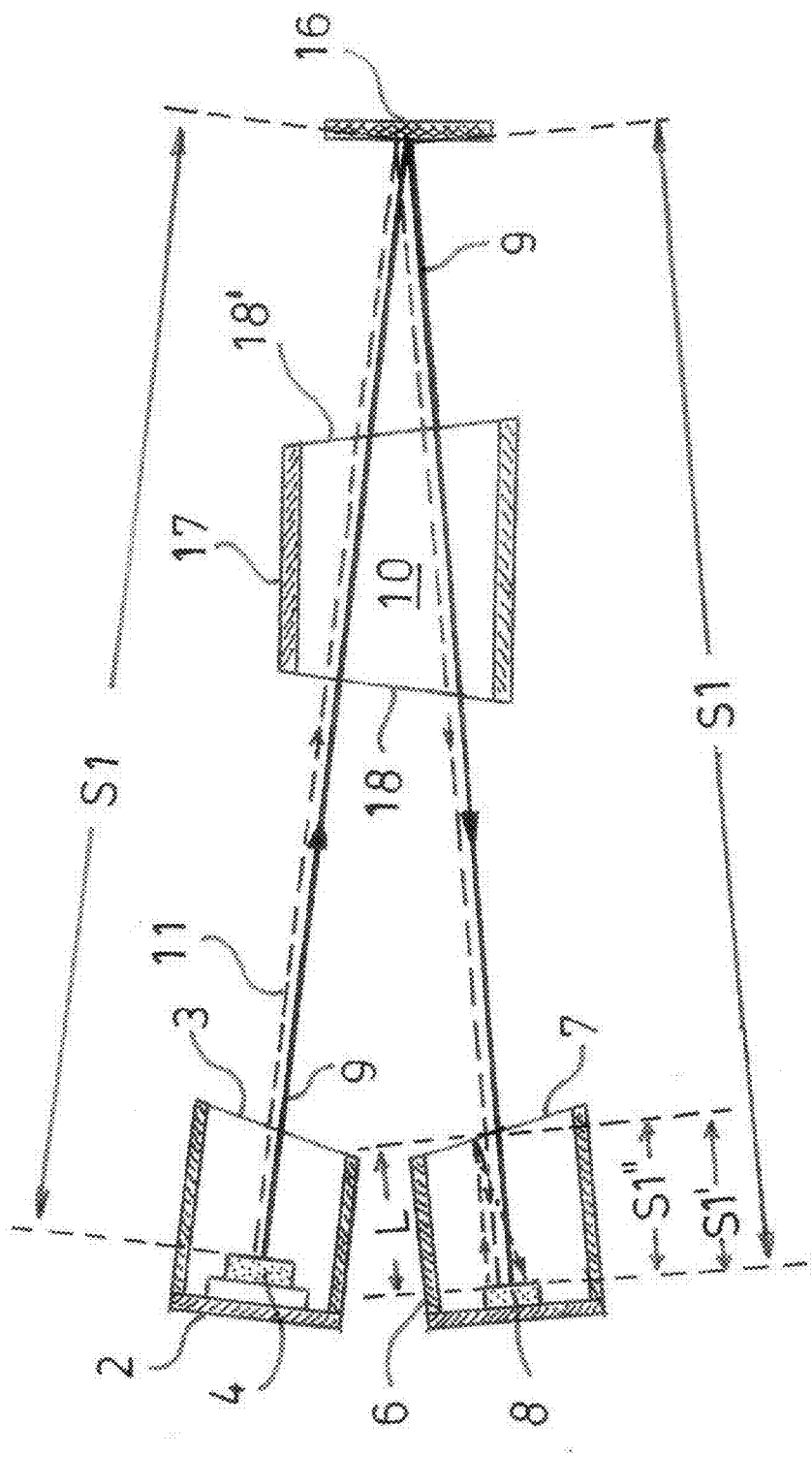

FIGS. 7a-7d illustrate in a schematic the optical path length $S_{Main}$ of the main light beam 9 and $S_{Scatter}$ of the scatter light beam 11, in case that at least one scatter light beam 11 partially reflected back in a direction of the light emitter 4 and/or the light detector 8 as a portion of the main light beam 9 through interference with the main light beam 9 leads to self-mixing in the light emitter 4 and/or to etalons at the light detector 8, this means its leads to an interfered main light beam 9. The scatter light beam 11 is thus directly or indirectly, this means at least deflected once, directed to the light emitter 4 or the light detector. For clarification purposes the light beams 9, 11 are illustrated located adjacent to one another though they actually coincide. FIGS. 7a-7d illustrate an embodiment in which the light detector 8 is arranged in a housing 6 adjacent to light emitter 4 received in a housing 2 and opposite there to a reflector 16 is arranged. FIGS. 7a, 7b illustrate the different optical path lengths of the scatter light beam $S_{Scatter}$ 11 in the housing 2, between the light emitter 4 and the housing window 3 of the housing 2 which interferes with the main light beam that is not illustrated and arranged in an interior of the light emitter (Laser diode). Alternatively the reflector 16 can be omitted when the housing 6 is positioned at the location of the reflector 16. Between the housing 2 with the housing window 3 and the housing 6 with the housing window 7 a gas cell 17 is arranged with two cell windows 18, 18', that are arranged opposite to one another wherein the gas cell is arranged at a distance from the housing 2, 6 and includes a gas or gas mix 10 that is to be detected. FIGS. 7c and 7d illustrate the different optical path lengths $S_{Main}$ of the main light beam 9 and $S_{Scatter}$ of the scatter light beam 11 up to the light detector 8 that is received in the housing 6.

FIG. 7a illustrates the light emitter 4, arranged at a distance L from the housing window 3 of the housing 2. The interfered main light beam 9 originating from the light emitter 4 reaches the light detector 8 passing through the optical path length 2*S1. The main light beam 9 emitted by the light emitter 4 is previously partially reflected back at the housing window 3 of the housing 2 in a direction of the light emitter 4 so that a scatter light beam 11 is formed. The scatter light beam 11 passes through the optical path length S1' from the light emitter 4 to the housing window 3 and back from the housing window 3 to the light emitter 4 the optical path length S1". The optical path lengths S1', S1" correspond to the distance L between the housing window 3 and light emitter 4. This yields an optical path $S_{Scatter}$ from the light emitter 4 to the housing window 3 and back to the light emitter 4 with $S_{Scatter}$=S1'+S1"=2L. Since per definition the main light beam 9 during self-mixing is completely in the light emitter (Laser) SMain=0 and $\Delta S = |S_{Scatter} - S_{Main}| = |S_{Scatter} - 0| = 2L$ is the path length difference.

In the light emitter 4 self-mixing occurs as an interference effect between the main light beam 9 and the scatter beam 11 so that the light detector 8 detects a measuring signal of the interfered main light beam 9 which includes a main signal portion and an interfering signal portion. The scatter light beam 11 is caused by the portion of the main light beam 9 that is emitted by the light emitter 4 and reflected back by the housing window 3. The light emitter 4 emits a non interfered main light beam 9 at the point in time of switch on, later it emits the main light beam 9 that is already interfered with the scatter light beam 11 in the interior of the light emitter 4. The interfered main light beam 9 passes the gas cell 17 and is then reflected back at the reflector 16 to the light detector 8, wherein the interfered main light beam 9 passes the two inclined cell windows 18, 18' twice. The self-mixing is performed in the light emitter 4 itself so that the optical path length difference $\Delta S$ in the housing 2 is defined as $\Delta S = |S_{Scatter} - S_{Main}|$, with $S_{Main}=0$, becomes $|S_{Scatter}|$ since the main light beam 9 only extends in the light emitter 4.

FIG. 7b also illustrates the light emitter 4 arranged at a distance L from the housing window 3 of the housing 2. The main light beam 9 emitted by the light emitter 4 is partially reflected at an inside of the housing window 3 of the housing 2 in a direction of a housing inner wall 19 of the housing 2 forming a scatter light beam 11. The scatter light beam 11 is then deflected at the housing inner wall 19 in a direction towards the light emitter 4 by additional scattering. The scatter light beam 11 thus covers the optical path length S1' from the light emitter 4 to the housing window 3 and then covers the optical path length S1''' from the housing window 3 to the housing inner wall 19 and from the housing inner wall to the light emitter 4 it covers the optical path length S1'. The optical path length S1' corresponds to the distance L between the light emitter 4 and the housing window 3. This yields an optical path length distance ΔS from the light emitter 4 to the housing window 3 and back to the light emitter 4, wherein ΔS=S1'+S1''+S1'''>2L. After the interference an interfered main light beam 9 exits from the light emitter 4, wherein the main light beam 9 is composed through self-mixing from the non interfered main light beam 9 and the scatter light beam 11 and reaches the light detector 8 over the optical path length 2*S1.

FIG. 7c illustrates the optical path length $S_{Main}$ of the main light beam 9 and the optical path length $S_{Scatter}$ for the scatter light beam 11 between the light emitter 4 and the light detector 8, in case that the modulated main light beam 9 originating from the light emitter 4 is partially scattered back on an outside in a direction of the light detector 8 wherein the back scattering is performed at the cell window 18 of the gas cell 17 oriented towards the housing 2, 6 while forming a scatter light beam 11. The main light beam 9 travels the optical path length $S_{Main}=2*S1$ from the light emitter 4 to the light detector 8. From the light emitter 4 to the cell window 18 the scatter light beam 11 travels the optical path length S1' and from the cell window 18 to the light detector 8 the scatter light beam travels the optical path length S1''. S1' and S1'' can thus be identical or different. The optical path length difference ΔS between the optical path length $S_{Main}$ of the main light beam 9 and the different optical path length $S_{Scatter}$ of the scatter light beam 11 between the light emitter 4 and light detector 8 is therefore defined by $\Delta S = S_{Main} - S_{Scatter} = 2*S1 - (S1'+S1'')$. Thus, an etalon occurs at the light detector 8 as an interference phenomenon between the main light beam 9 and scatter light beam 11 in the form of an interfered main light beam 9, which is composed of the non interfered main light beam 9 and the scatter light beam 11 so that the light detector 8 includes a measuring signal with a main signal and an interfering signal.

FIG. 7d illustrates the optical path length $S_{Main}$ of the main light beam 9 and the optical path length $S_{Scatter}$ of the scatter light beam 11 between the light emitter 4 and the light detector 8, in case that the modulated main light beam 9 originating at the light emitter 4 is not partially scattered back at the cell window 18 oriented towards the housing 2, 6 on an outside in a direction towards the light detector 8 forming a scatter light beam 11, but is only partially scattered back by the aperture of the light detector 8 (photo diode) in a direction of the housing window 7 of the light detector 8. The housing window 7 reflects or scatters the scatter light beam 11 back in a direction of the photo diode 8. Thus, an interference occurs between the main light beam 9 and the scatter light beam 11 so that an interfered main light beam 9 that includes these beams is formed. The main light beam 9 and the scatter light beam 11 travel the optical path $S_{Main}-S_{Scatter}=2*S1$ from the light emitter 4 to the light detector 8. The main light beam 9 is partially reflected back to the light detector 8 in a direction towards the housing window 7. Thus, the scatter light beam 11 travels the additional optical path length S1' from the light detector to the housing window 7 and from the housing window 7 to the light detector 8, it travels the optical path length S1''. The optical path lengths S1', and S1'' correspond to the distance L between the light detector 8 and the housing window 7. This yields an optical path length difference ΔS between the main light beam 9 and the scatter light beam 11, wherein $\Delta S = |(2*S1)-(2*S1+S1'+S1'')|=S1'+S1''=2L$, so that the light detector 8 receives a measuring signal with main signal and an interfering signal.

Typically optical measuring systems of this type have scatter light beams 11 and thus interferences with the respective main light beam 9 according to FIGS. 7a-7d in combination wherein the main signal and the interfering signal superimpose through the reference phenomenon and lead to an interfered measuring signal of the light detector. Through a suitable choice of the distance between the optically effective boundary surfaces of the respective optical and/or opto-mechanical components of the optical measuring system the influence of the interfering signal upon the measuring signal can be significantly reduced. FIG. 1 illustrates a variant similar to FIG. 7a which is not illustrated in FIGS. 7a-7d. In the variant according to FIG. 1 the housing 6 is positioned at the location of the reflector 16 and replaces the reflector 16. Also the gas cell 17 is not illustrated. Thus, the main light beam 9 is partially reflected at the housing window 3 of the housing 2 with the light emitter 4 forming a scatter light beam 11 which extends in a direction towards the light emitter. At the housing window 7 of the housing 6 with the light detector 8 respective scatter light beams can be generated which, however, are not illustrated. The main light beam 9 is reflected or scattered at an inside 12 and at an outside 13 of the housing window 3. The housing window 3 has a thickness 14 which is defined by the distance of the inside 12 from the outside 13 of the housing window 3. The light emitter 4, light detector 8 and the two housing windows 3, 7 form optical and/or opto-mechanical components 15 of the optical measuring systems 1. The scatter light beam 11 reflected out of the main light beam 9 in a direction towards the light emitter 4 causes a measuring signal through mixing with the main light beam in the laser wherein the measuring signal includes an interfering signal and a main signal. Thus, the light emitter 4 is arranged with its aperture at a defined distance L from the housing window 3, wherein the distance L changes the optical path length difference ΔS=2*L and influences the amplitude and the period Λ of the interfering signal caused in the measuring signal by the housing window 3.

The effect of an interference upon the measuring signal is subsequently described in an exemplary manner based on three different distances L between the aperture of the light emitter 4 and a scattering window inside 12 with respect to FIGS. 2a-2c and 3a-3c. Herein the case illustrated in FIG. 7a for direct back scattering is considered. The first distance L=0.3 cm (FIG. 2a, 3a) approximately corresponds to the distance between the light emitter 4 and the window inside 12. The distance L=0.584 cm (FIG. 2b, 3b) was selected in order to demonstrate the worst case, this means to generate an interfering signal that has a period Λ in the order of magnitude of the typical width of a gas absorption line. With L=1.17 cm (FIGS. 2c, 3c) a case is demonstrated where there is no interference, this means no interfering signal in the demodulated measuring signal. The illustrations are based on a triangular wave form with a fixed modulation width Δλ=0.195 mm at $\lambda_0$=1.512 μm.

Figure 2A:
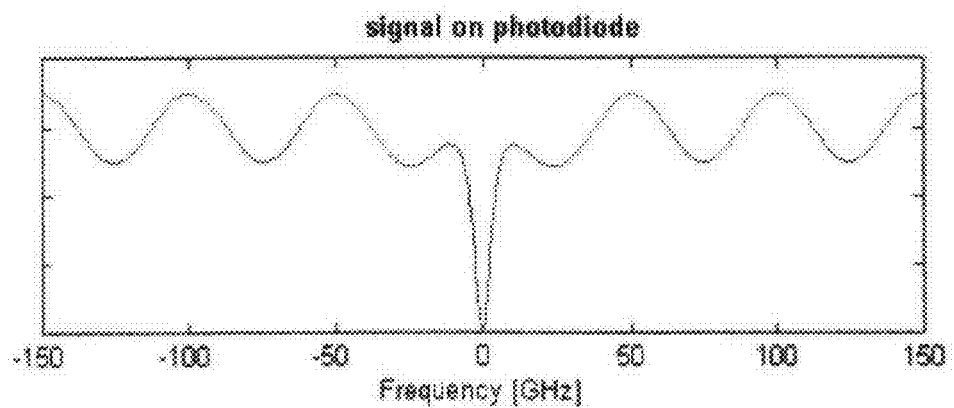
FIGS. 2a-2c illustrate a super position of the measuring signal by interference (self-mixing) of the main-and scatter light beams for three different distances between the light emitter and the housing window for a modulation of the main light beam through a triangular wave form.
Figure 2B:
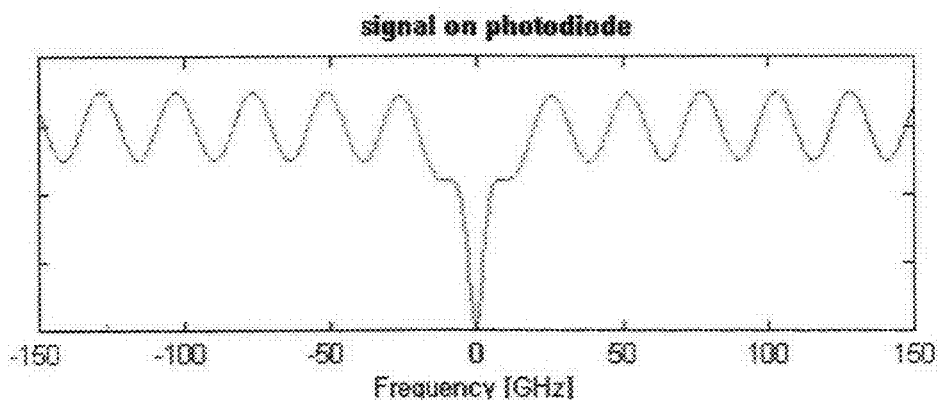
Figure 2C:
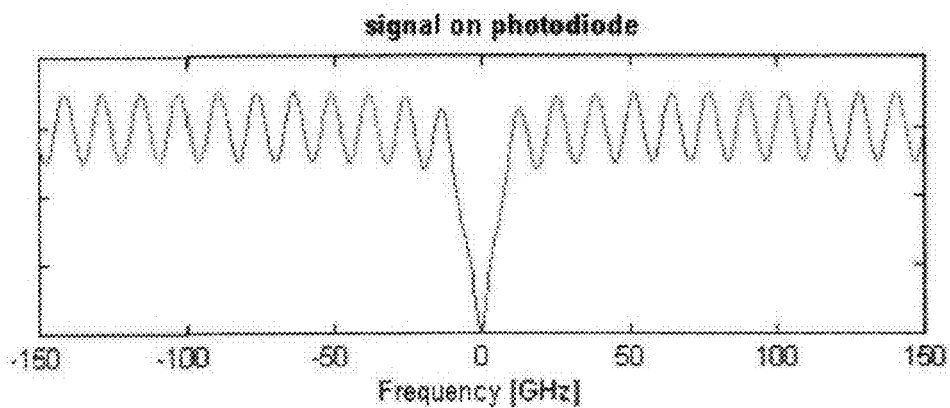

FIGS. 2a-2c illustrate the simulated measuring signal of the light detector 8 for the three distances L, or the optical path length differences ΔS=2*L. The simulated measuring signal is the standardized power of the light emitter in range of 0.9985-1.000. The figures shall illustrate the different curve shapes. The peak at 0 GHz represents the actual signal of the absorption that is to be measured, in this case the signal of a NH$_3$ gas peak with Lorentz profile which is now superimposed by the periodic interference. It is apparent that the period Λ decreases with increasing distance L, this means with increasing optical path length S$_{Scatter}$ for the scatter light beam 11. The amplitude of the interference is the same for all three variants since the reduction of the back coupling with increasing distance L of the housing window 3 with respect to the light emitter 4 is not considered in the respective figures.

Figure 3A:
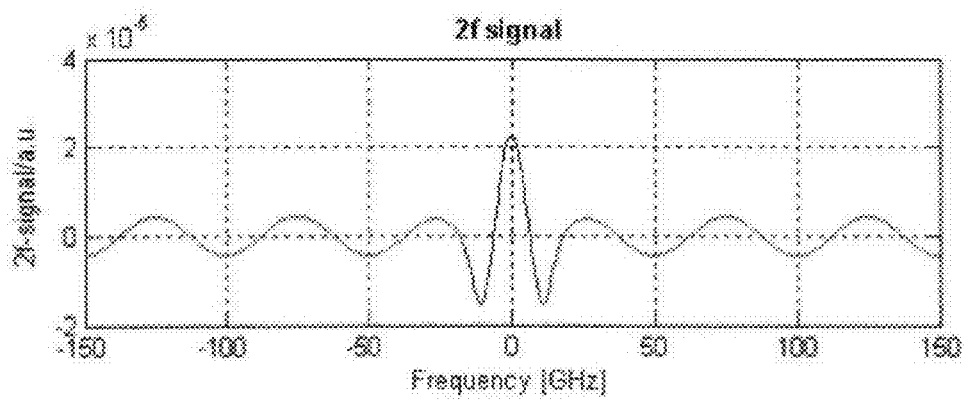
FIGS. 3a-3c illustrate effects of the variation of the distance between the light emitter and the housing window according to FIG. 2 upon the 2f-signal derived from the measuring signal of the detector.
Figure 3B:
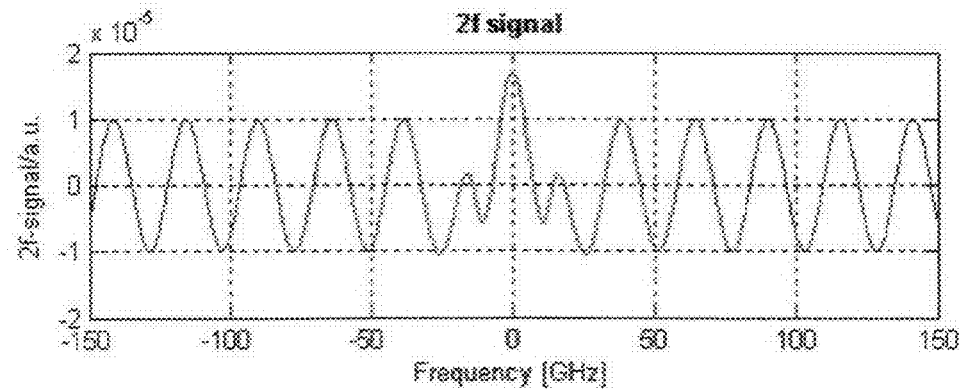
Figure 3C:
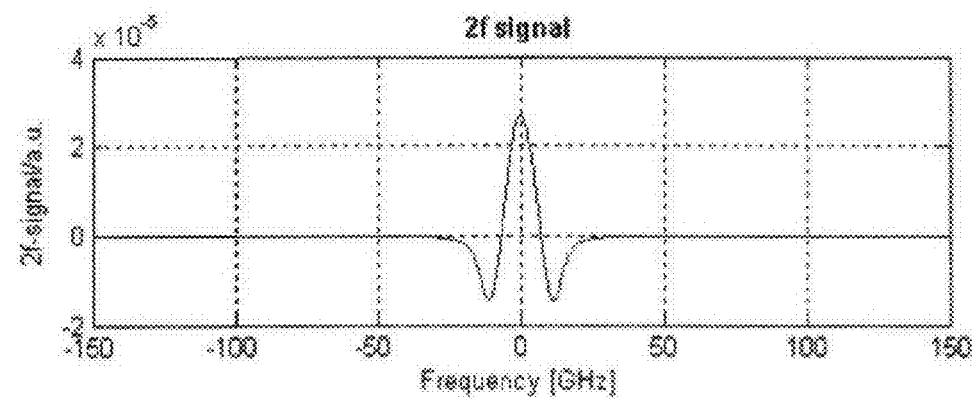

FIGS. 3a-3c illustrate the effect upon the 2f-signal derived from the measuring signal, this means at m=2. These figures illustrate the amplitudes of the respective interferences of the 2f-measuring signal relative to the three different optical path lengths S$_{Scatter}$ for the scatter light beam 11, this means at different distances between the aperture of the light emitter 4 and the housing window 3. It is apparent that the interfering signal increases strongly from L=0.3 cm (FIG. 3a) to L=0.584 cm (FIG. 3b) and drops off very quickly thereafter. The illustration with L=0.3 cm shows in particular that the interference is also visible in the 2f-signal. This interference limits measuring precision for the optical measuring system 1. When the distance L is extended to L=0.584 cm (FIG. 3b), the effect is amplified and the NH$_3$ gas signal can be hardly differentiated from the interferences. However, a significant reduction of the measuring error can only be achieved when the distance L between the housing window 3 and the light emitter 4 is selected so that the condition $\Delta S=2*\lambda_0^2/\Delta\lambda 2*\Delta X$ is fulfilled for the optical path length differences ΔS. For the distance L with L=1.17 cm (FIG. 3c) the measuring signal only shows the signal of the NH$_3$ peak, this means the 2f-signal is completely free from interference.

Figure 4:
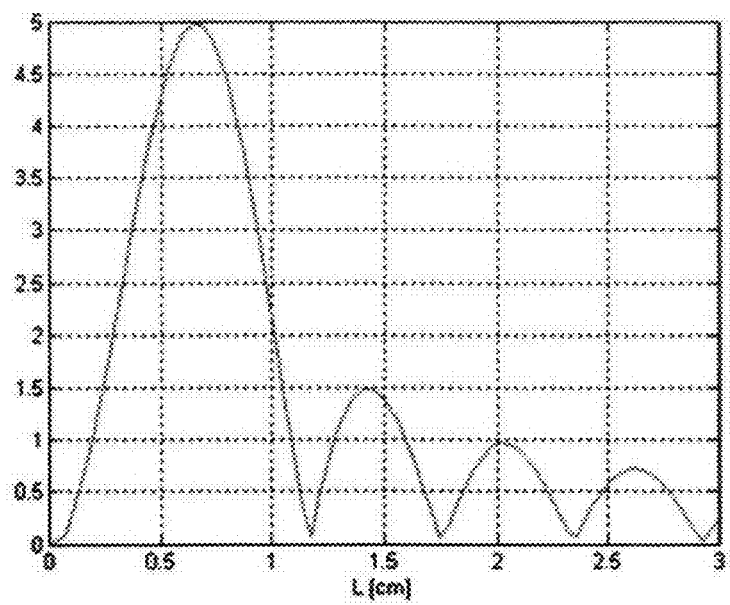
FIG. 4 illustrates the amplitude of the interfering signals in the 2f-Signal with reference to the distance determining the optical path length difference at a modulation of the main light beam with a triangular wave form.

FIG. 4 illustrates the amplitude A of the interfering signal as a function of the distance L in the 2f-measuring signal for the case illustrated in FIG. 7a for direct back coupling. The Fourier-component of the demodulated measuring signal is illustrated. The illustrated intensity curve includes hump shaped intensity portions which include a main maximum with a highest amplitude-peak and a number of intermediary maxima with respectively reduced amplitude peaks. The large first main maximum and the subsequent zero points and smaller intermediary maxima are clearly visible. Thus, the main maximum starts as a first portion at the zero point (L=0 cm), wherein the intermediary maxima adjoin at the right of the main maximum. It is apparent that the interfering signal increases greatly from L=0 cm to L=0.584 cm and subsequently drops off quickly and reaches the first local minimum at $L=\Delta S/2=\lambda_0^2/\Delta\lambda=\Delta X$.

Figure 5:
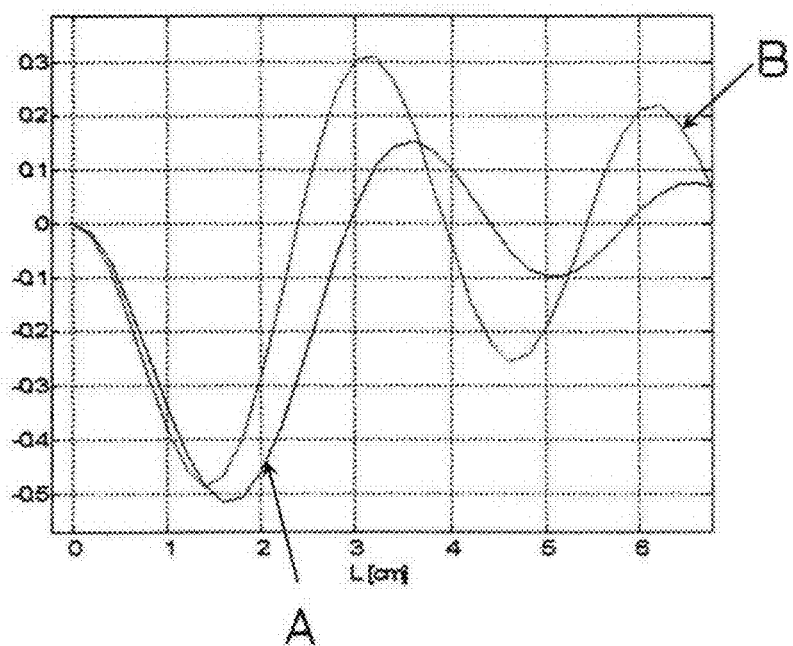
FIG. 5 illustrates a comparison the zero passages of the measuring signal for a triangular wave form (A) and a cosine shaped wave form (B) as a function of a distance between the light emitter and the housing window with a constant modulation span.

FIG. 5 illustrates a comparison of the dependency of the zero passages of the amplitude of the demodulation measuring signal at an identical modulation span Δλ for a triangular wave form (curve A) and a cosine shaped wave form (Curve B). The triangular modulation dampens the interfering signal portion of the demodulated measuring signal stronger than the cosine modulation, however compared to the cosine modulation it requires slightly larger distances between the light emitter 4 and the optical and/or opto-mechanical components 15, like e.g. the housing window 3, which can cause scatter light beams 11.

Figure 6:
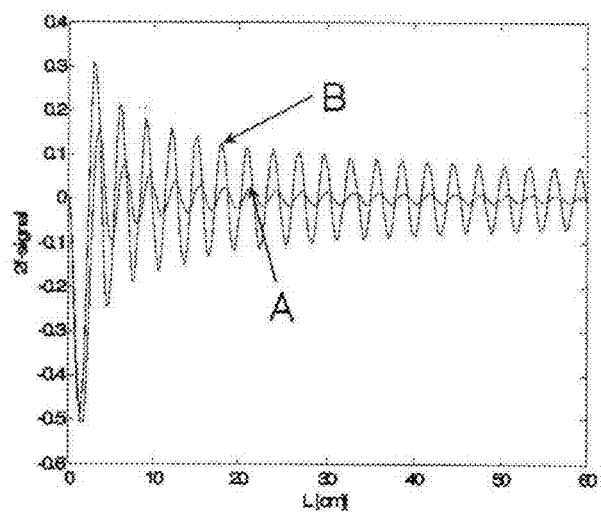
FIG. 6 illustrates a comparison of the amplitude dependency of the 2f-signal from the distance between an optical or opto-mechanical component and the light emitter with a triangular wave form (A) and a cosine shaped wave from (B)

FIG. 6 illustrates a comparison of the amplitude dependency of the 2f-signal from the distance L between the light emitter 4 and an opto-mechanical component 15 when modulating the main light beam with a triangular wave form (curve A) and a cosine shaped wave form (curve B). It is clearly visible that the triangle modulation is more effective also here than the cosine modulation. The influence of the interfering signal decreases much faster in intensity in the triangle modulation with increasing distance between light emitter 4 and optical and/or opto-mechanical components 15, which can cause scatter light beams 11, like e.g. the housing window 3. The figure shows that during triangle shaped modulation the optical interference decreases much faster with the removal of the opto-mechanical element, than for the cosine shaped modulation. Thus the influence of the interference proximal to the light emitter (Laser diode), e.g. at the housing window 3 of the light emitter 4, which is for example removed by 1.8 cm from the laser diode, upon both curves A and B is almost identical however for scattering at the cell window 18 of the gas cell 17, which is for example 5 cm away is already greatly reduced. For an influence of an interference at the light detector 8 which is for example 60 cm away from the light emitter 4, the difference is significant.

Generally plural back couplings of this type are possible and typically between also provided between the light emitter 4 and one of the other opto-mechanical components 15 at the optical measuring system 1 with different optical path lengths S$_{Scatter}$. For each individual optical path length S$_{Scatter}$ the conditions recited supra shall be fulfilled in an ideal case. In practical applications this is often not possible or only possible within limits because between the different optical path lengths S$_{Scatter}$, S$_{Main}$, this means the path lengths that are caused by different distances L of the respective components 15, there are generally certain dependencies. A practical condition for positioning an optical or mechanical component 15, which causes scatter radiation relative to the light emitter 4, is for example:

$$|S_{Scatter}-S_{Main}|=\Delta S>\lambda_0^2/\Delta\lambda,$$

wherein $\lambda_0$ is the mean wave length and Δλ is the modulation span of the modulated main light beam 9 in nanometers. Fulfilling this condition is advantageous since the interfering signal between an optical path length difference ΔS or $\Delta S'=\lambda_0^2/\Delta\lambda$ and $2*\lambda_0^2/\Delta\lambda$ decreases by a large amount. The symbol ΔS' in case of several sources for scatter light beams 11, this means of plural reflecting or back scattering optical or opto-mechanical components 15 and/or of plural reflecting or back scattering surfaces of a component 15 of this type, which are arranged at a different distance L from the light emitter 4 and thus cause plural differing optical path lengths S$_{Scatter}$ of the scatter light beams 11 provide the shortest optical path length difference ΔS' which provides a relevant contribution to the interference of the main light beam 9 with the scatter light beam 11. It is furthermore evident that the local maxima of the interference become smaller and smaller with increasing path length difference ΔS. This effect is further amplified in that the back coupled light becomes less and less with increasing distance (not considered in FIG. 4).

In practical engineering applications the tolerances of the relative positions of the optical and/or opto-mechanical components 15, 4, 8 have to be considered. In principle the housing window 3 has the problem that the distance L to the inside 12 of the housing window 3 and to its outside 13 has to be optimized at the same time in order to achieve and optimum result. For this there are two solutions in principle in order to comply with the requirement in spite of the different optical path length S$_{Scatter}$ and the resulting optical path length differences ΔS which are caused by the uneven distance L of the inside 12 and the outside 13 from the light emitter 4, that both are at a minimum of the curve A(L). This can be achieved either by adapting the thickness 14 of the housing window 3 and/or tilting the housing window 3 with respect to the beam path.

Also inserting an optical isolator into the beam path that is not illustrated in the figures is helpful, wherein the insulator provides that back scattered light from subsequent optical elements 15 cannot cause self-mixing anymore. The first boundary surface of the optical insulator that is arranged in the beam direction of the light emitter 4, for example a lambda-quarter-plate, still causes scatter radiation which can cause self-mixing. Therefore it is advantageous to optimize the position of this first optical boundary surface according to the spacing rules provided supra. In an embodiment a lambda-quarter-late can be applied at the inside 12 of the housing window 3 wherein the lambda-quarter-plate turns back reflected light from the outer side, for example from the outside 13 or from the housing window 7 of the housing 6 with the light detector 8 by an angle of 90° so that it cannot interfere with the main light beam 9 of the light emitter 4 or optional scatter light beams 11 in the housing 2 in which the light emitter 4 is arranged. Thus, it is advantageous to connect the optical insulator without any offset directly and flat with the inside 12 with a glue, whose refractive index closely matches the refractive index of the insulator or of the housing window 3 so that no additional optical boundary layer is created between the optical insulator and the housing window. Alternatively for example the lambda-quarter-plate can be used as a housing window 3.

Figure 8:
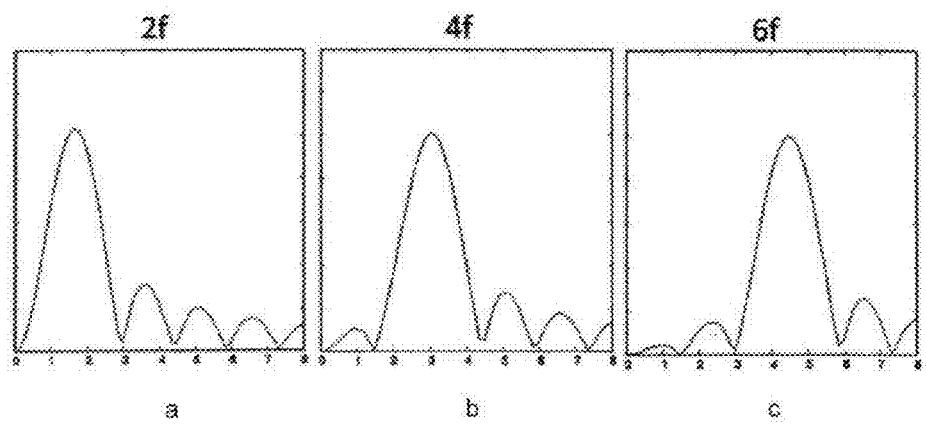
FIG. 8 illustrates the distance dependent amplitude of the interfering signal for a 2f-signal (FIG. 8a), a 4f-signal (FIGS. 8b) and 6f-signal (FIG. 8c), respectively for a modulation of the main light beam with a triangular wave form.

In FIG. 8 the distance dependent amplitude of the interfering signal is illustrated for a 2f-Signal (FIG. 8*a*), a 4f-signal (FIG. 8*b*) and a 6f-Signal (FIG. 8*c*), respectively for a modulation of the main light beam 9 with a triangular wave form. FIGS. 8*a-c* illustrate the interfering signals A (L) as a function of the distance L or of the optical path length difference ΔS. The large main maximum and the smaller intermediary maxima adjoining at the left and/or right with the zero points arranged there between are clearly visible. The position of the main maximum relative to the intermediary maxima is a function of the order of the demodulated mf-measuring signal that is being used. For a 2f-signal (FIG. 8*a*) the main maximum begins as a first portion at the zero point, wherein the intermediary maxima adjoin at a right side at the main maximum, for a 4f-Signal (FIG. 8*b*) an additional intermediary maximum is arranged between the zero point and the main maximum, for a 6f-signal (FIG. 8*c*) two intermediary maximal are arranged on a left side of the main maximum. The position of the main maximum is defined by the order m/2 of the demodulated measuring signal that is being used. On the right side of the main maximum a number of intermediary maxima is also arranged for the 4f-signal and the 6f-signal.

In practical applications the laser package is often sealed hermetically tight so that the inside of the window will not contaminate during the entire service life. In this case it is sufficient to provide that the inside of the window is optically clean so that in this case scatter light beams from the inside can be neglected and the configuration can be adapted to the outside of the window which contrary to the inside is very prone to contaminate.

A typical method when optimizing a wave length modulated measuring system includes initially a definition of the wave length range that is being used, adapted to the spectrum to be measured, then definition of the signal processing method and optimization of the modulation span Δλ that is being used with respect to noise, transversal sensitivities and similar and subsequently a computation of optimum positions of all optical or opto-mechanical components 15 of the optical measuring system 1 for measuring a spectrum. After the position of the optical and optical and opto-mechanical components 15 has been determined for the first time a fine optimization of the modulation span Δλ can be performed optionally in order to compensate for manufacturing tolerances.

What is claimed is:

1. An optical measuring system for gas detection, the optical measuring system comprising:

a light emitter and at least one light detector forming optical components that are arranged in at least one housing; and housing windows provided at the at least one housing and forming opto-mechanical components; or other opto-mechanical components, wherein the opto-mechanical components or the other opto-mechanical components include optically effective boundary surfaces, wherein the light emitter emits a modulated main light beam with a mean wave length $\lambda_0$ with a modulation span Δλ, wherein at least one scatter light beam that is partially reflected or scattered from the main light beam at least at one optically effective boundary surface of at least one opto-mechanical component in a direction of the light emitter or of the light detector causes self-mixing in the light emitter or etalons at the light detector through interference with the main light beam, wherein the interference causes an interfered main light beam so that a measuring signal of the light detector includes an interfering signal portion and a main signal portion, wherein the interfering signal portion influences a demodulated measuring signal put out by the light detector, wherein at least one of the optical or opto-mechanical components is/are arranged relative to another optical or opto-mechanical component so that an optical path length difference ΔS for the main light beam and the scatter light beam is caused by a spatial orientation or distance of optically effective boundary surfaces of the optical or opto-mechanical components relative to one another, wherein the optical path length difference ΔS is defined by a difference between an optical path length $S_{Main}$ of the main light beam and an optical path length $S_{Scatter}$ of the scatter light beam, wherein the optical path length difference ΔS cancels or minimizes an effect of the interfering signal upon the main signal for a demodulated measuring signal for all phases at the selected modulation span Δλ of the main light beam having the wave length $\lambda_0$, wherein a period Λ of the demodulated measuring signal results from the optical path length difference ΔS, wherein the period Λ is caused by the interfering signal portion caused by the at least one optical or opto-mechanical component through interference with the main signal, and wherein the modulation of the main light beam is made with any periodic wave form and the modulation span Δλ is the peak to peak amplitude of the modulation signal used for modulating the main light beam of the wave length $\lambda_0$.

2. The optical measuring system according to claim 1, wherein the optical path length difference ΔS is greater than 0.5*ΔX*(m+1), with m=2, 4, 6, . . . , according to the order 2f, 4f, 6f, . . . of the employed measuring signal, and wherein ΔX is a distance where a Fourier-component of the demodulated measuring signal adjacent to a highest amplitude-peak is repeatedly minimal.

3. The optical measuring system according to claim 1, wherein the optical path length difference ΔS is greater than 0.7 times or less than 1.3 times of n*ΔX, with n=1, 2, 3, ..., and with n≠m/2, with m=2, 4, 6, ..., according to the order 2f, 4f, 6f, ... of the employed measuring signal, and wherein ΔX is a distance where a Fourier-component of the demodulated measuring signal adjacent to a highest amplitude-peak is repeatedly minimal.

4. The optical measuring system according to claim 3, wherein the optical path length difference ΔS is greater than 0.8 times or less than 1.2-times of n*ΔX.

5. The optical measuring system according to claim 3, wherein the optical path length difference ΔS is equal to n*ΔX.

6. The optical measuring system according to claim 1, wherein the main light beam is modulated by a triangular wave form.

7. The optical measuring system according to claim 6, wherein ΔX is $\lambda_0^2/\Delta\lambda$.

8. The optical measuring system according to claim 1, wherein a distance of an inside of a provided housing window of the light emitter from the light emitter or a distance of an inside of a housing window of the light detector from the light detector is at least 8 mm, at least 10 mm, or at least 15 mm.

9. A method for gas detection, comprising the steps:

using an optical measuring system including a light emitter and at least one light detector forming optical components that are arranged in at least one housing, and housing windows provided at the at least one housing and forming opto-mechanical components, or other opto-mechanical components including optically effective boundary surfaces;

emitting a modulated main light beam with a mean wave length $\lambda_0$ and with a modulation span Δλ from the light emitter;

receiving the main light beam in the at least one light detector after passing it through a gas or gas mix;

causing self-mixing in the light emitter or etalons at the light detector by at least one scatter light beam that is partially reflected or scattered from the main light beam at least at one optically effective boundary surface of the at least one opto-mechanical component in a direction of the light emitter or of the light detector through interference with the main light beam;

forming an interfered main light beam through the interference so that the light detector generates a measuring signal including an interfering signal portion and a main signal portion, wherein a demodulated measuring signal put out by the light detector is negatively influenced by the interfering signal, wherein at least one of the optical or opto-mechanical components is/are arranged relative to another optical or opto-mechanical component so that an optical path length difference ΔS for the main light beam and the scatter light beam is caused by a spatial orientation or distance (L) of optically effective boundary surfaces of the optical or opto-mechanical components relative to one another, wherein the optical path length difference ΔS is defined by a difference between an optical path length $S_{Main}$ of the main light beam and an optical path length $S_{Scatter}$ of the scatter light beam, wherein the optical path length difference ΔS cancels or minimizes an effect of the interfering signal upon the main signal for a demodulated measuring signal for all phases at the selected modulation span Δλ of the main light beam of the wave length $\lambda_0$, wherein a period Λ of the demodulated measuring signal results from the optical path length difference ΔS, wherein the period Λ is caused by the interfering signal caused by the at least one optical or opto-mechanical component through interference with the main signal, and wherein the modulation of the main light beam is made with any periodic wave form and the modulation span Δλ is the peak to peak amplitude of the modulation signal used for modulating the main light beam of the wave length $\lambda_0$.

10. The method according to claim 9, wherein the optical path length difference ΔS is greater than 0.5*ΔX*(m+1), with m=2, 4, 6, ..., according to the order 2f, 4f, 6f, ... of the employed measuring signal, and wherein ΔX is a distance where a Fourier-component of the demodulated measuring signal adjacent to a highest amplitude-peak is repeatedly minimal.

11. The method according to claim 9, wherein the optical path length difference ΔS is greater than 0.7 times or less than 1.3 times of n*ΔX, with n=1, 2, 3, ..., and with n≠m/2, with m=2, 4, 6, ..., according to the order 2f, 4f, 6f, ... of the employed measuring signal s, and wherein ΔX is a distance where a Fourier-component of the demodulated measuring signal adjacent to a highest amplitude-peak is repeatedly minimal.

12. The method according to claim 11, wherein the optical path length difference ΔS is greater than 0.8 times or less than 1.2 times of n*ΔX.

13. The method according to claim 11, wherein the optical path length difference ΔS is equal to n*ΔX.

14. The method according to claim 9, wherein the main light beam is modulated by a triangular wave form.

15. The method according to claim 14, wherein ΔX is $\lambda_0^2/\Delta\lambda$.

16. An optical measuring system for gas detection, the optical measuring system comprising:

a light emitter and at least one light detector forming optical components that are arranged in at least one housing; and housing windows provided at the at least one housing and forming opto-mechanical components; and other opto-mechanical components, wherein the opto-mechanical components and the other opto-mechanical components include optically effective boundary surfaces, wherein the light emitter emits a modulated main light beam with a mean wave length $\lambda_0$ with a modulation span Δλ, wherein at least one scatter light beam that is partially reflected or scattered from the main light beam at least at one optically effective boundary surface of at least one opto-mechanical component in a direction of the light emitter and of the light detector causes self-mixing in the light emitter and etalons at the light detector through interference with the main light beam, wherein the interference causes an interfered main light beam so that a measuring signal put out by the light detector includes an interfering signal portion and a main signal portion, wherein the interfering signal portion influences a demodulated measuring signal of the light detector, wherein at least one of the optical and opto-mechanical components are arranged relative to another optical and opto-mechanical component so that an optical path length difference $\Delta S$ for the main light beam and the scatter light beam is caused by a spatial orientation and distance (L) of optically effective boundary surfaces of the optical and opto-mechanical components relative to one another, wherein the optical path length difference $\Delta S$ is defined by a difference between an optical path length $S_{Main}$ of the main light beam and an optical path length $S_{Scatter}$ of the scatter light beam, wherein the optical path length difference $\Delta S$ cancels or minimizes an effect of the interfering signal upon the main signal for a demodulated measuring signal for all phases at the selected modulation span $\Delta \lambda$ of the main light beam having the wave length $\lambda_0$, wherein a period $\Lambda$ of the demodulated measuring signal results from the optical path length difference $\Delta S$, wherein the period $\Lambda$ is caused by the interfering signal portion caused by the at least one optical or opto-mechanical component through interference with the main signal, and wherein the modulation of the main light beam is made with any periodic wave form and the modulation span $\Delta \lambda$ is the peak to peak amplitude of the modulation signal used for modulating the main light beam of the wave length $\lambda_0$.

17. A method for gas detection, comprising the steps:

using an optical measuring system including a light emitter and at least one light detector forming optical components that are arranged in at least one housing, and housing windows provided at the at least one housing and forming opto-mechanical components, and other opto-mechanical components including optically effective boundary surfaces;

emitting a modulated main light beam with a mean wave length $\lambda_0$ and with a modulation span $\Delta \lambda$ from the light emitter;

receiving the main light beam in the at least one light detector after passing it through a gas or gas mix;

causing self-mixing in the light emitter and etalons at the light detector by at least one scatter light beam that is partially reflected or scattered from the main light beam at least at one optically effective boundary surface of the at least one opto-mechanical component in a direction of the light emitter and of the light detector through interference with the main light beam;

forming an interfered main light beam through the interference so that the light detector generates a measuring signal including an interfering signal portion and a main signal portion, wherein a demodulated measuring signal put out by the light detector is negatively influenced by the interfering signal, wherein at least one of the optical and opto-mechanical components is arranged relative to another optical and opto-mechanical component so that an optical path length difference $\Delta S$ for the main light beam and the scatter light beam is caused by a spatial orientation or distance of optically effective boundary surfaces of the optical and opto-mechanical components relative to one another, wherein the optical path length difference $\Delta S$ is defined by a difference between an optical path length $S_{Main}$ of the main light beam and an optical path length $S_{Scatter}$ of the scatter light beam, wherein the optical path length difference $\Delta S$ cancels or minimizes an effect of the interfering signal upon the main signal for a demodulated measuring signal for all phases at the selected modulation span $\Delta \lambda$ of the main light beam of the wave length $\lambda_0$, wherein a period $\Lambda$ of the demodulated measuring signal results from the optical path length difference $\Delta S$, wherein the period $\Lambda$ is caused by the interfering signal caused by the at least one optical or opto-mechanical component through interference with the main signal, and wherein the modulation of the main light beam is made with any periodic wave form and the modulation span $\Delta \lambda$ is the peak to peak amplitude of the modulation signal used for modulating the main light beam of the wave length $\lambda_0$.

* * * * *